US00PP18370P3

(12) United States Plant Patent
Gerawan

(10) Patent No.: US PP18,370 P3
(45) Date of Patent: Dec. 25, 2007

(54) APRICOT TREE NAMED 'GA 10F'

(50) Latin Name: *Prunus armeniaca*
Varietal Denomination: GA 10F

(76) Inventor: Mike Gerawan, 21249 E. Jefferson, Reedley, CA (US) 93654

( * ) Notice: Subject to any disclaimer, the term of this patent is extended or adjusted under 35 U.S.C. 154(b) by 17 days.

(21) Appl. No.: 11/312,165

(22) Filed: Dec. 19, 2005

(65) Prior Publication Data

US 2007/0143884 P1 Jun. 21, 2007

(51) Int. Cl.
*A01H 5/00* (2006.01)

(52) U.S. Cl. ..... Plt./186
(58) Field of Classification Search ..... Plt./186
See application file for complete search history.

*Primary Examiner*—Kent Bell
*Assistant Examiner*—Annette H Para
(74) *Attorney, Agent, or Firm*—Townsend and Townsend and Crew LLP

(57) ABSTRACT

This present invention relates to an apricot tree, *Prunus armeniaca,* and more specifically to a new and distinct variety broadly characterized by a medium size vigorous, semi hardy with good production. This tree does need pollinization. 'Castlebright' and 'Patterson' are apricot varieties (unpatented) and are usually equally as pollenized. Under the environmental conditions in Central California San Joaquin Valley the fruit matures in mid May, 2005. The fruit is medium sized, with good orange color, orange yellow flesh color, firm with a good flavor. The fruit matures at least 10 days before the 'Patterson' variety, having more red blush on mature fruit. This variety is a second generation seedling of unknown parentage.

1 Drawing Sheet

Latin name of the genus and species: The apricot cultivar of this invention is botanically identified as *Prunus armeniaca.*

Variety denomination: The variety denomination is 'GA 10F'.

BACKGROUND OF THE INVENTION

In an effort to improve and to develop promising varieties of fruit for the consuming parties, fruit tree stock are planted in nurseries for examination and evaluation of different selections of apricot, peach and plum each year. The present invention represents an apricot seedling of unknown parentage that was discovered in April 1999. This new invention produced fruit early in maturing, possessed good size color and flavor. The seedling was asexually reproduced by budding on Citation (peach/plum hybrid) rootstock in 2000. The resulting trees were planted in the current location reproducing the fruit and plants that are in all respects possess all of the characteristics of the original plant. The present variety of freestone in type produces fruit days earlier than 'Castlebright' or 'Patterson' varieties with a higher degree of color. More specifically, the fruit matures at least 10 days before the 'Patterson' variety, having more red blush on mature fruit.

BRIEF SUMMARY OF THE INVENTION

The present variety of apricot is characterized by a medium size, vigorous, good color, good flavor and is a good producer. The variety does not pollination by another variety of apricot. The fruit matures under the growing conditions in the Central San Joaquin Valley of Central California in mid May, 2005.

DETAILED DESCRIPTION OF THE INVENTION

Figure 1:
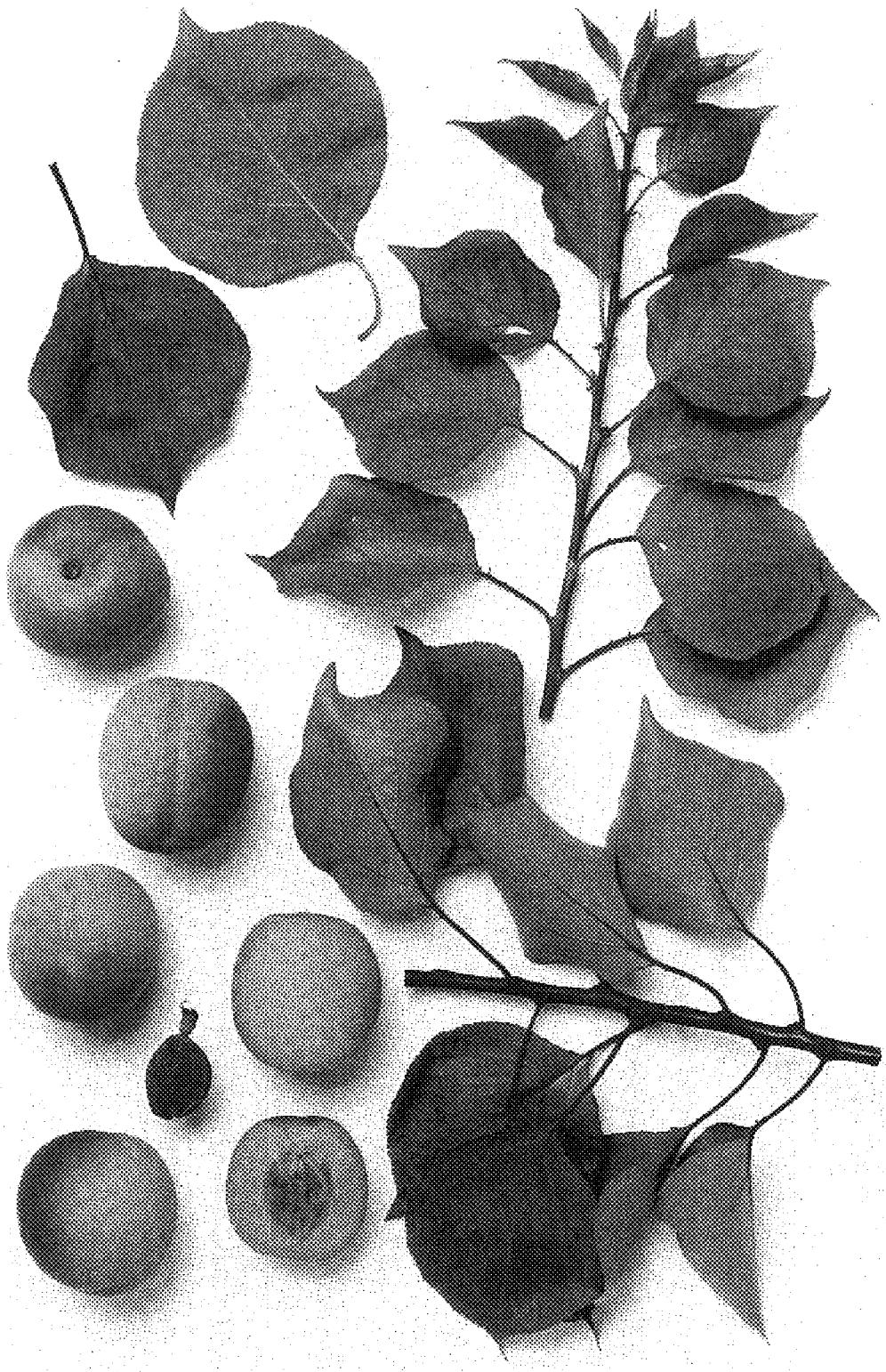
FIG. 1 illustrates, clockwise from top left: the front and back of whole leaves, whole leaves on a twig from a twig end, whole leaves on a twig from a twig mid-section, pit cavity, pit, and various views of the fruit displaying the characteristic skin color, shape, and color of the flesh.

Referring more specifically to the pomological characteristics of this new and distinct apricot tree the following have been observed under the environmental conditional conditions prevailing near Reedley, Fresno County (San Joaquin), Calif. and was selected at the start of shipping ripe on May 14, 2005. All major color code designations are taken from Dictionary of Color, Maerz and Paul, First Edition, 1930. Common color names are also used occasionally.

Tree:
- *Size.*—Medium — 8–10 feet high, 5–7 feet wide at 4th leaf.
- *Vigor.*—Good.
- *Growth (shape) figure.*—Upright and spreading.
- *Hardy.*—Normal for apricots in the Central San Joaquin Valley.
- *Productivity.*—Very good.

Trunk:
- *Size.*—Medium — 15 inches in circumference, 12 inches above ground.
- *Texture.*—Semi rough.
- *Bark color.*—P1.46 H5 Near Old Mauve.
- *Lenticels.*—Scattered on trunk, small.

Branches:
- *Size.*—Moderate — 5 inches in circumference, 24 inches above crotch, angle of branches — approximately 37°.
- *Surface.*—Texture — mature — nearly smooth immature — smooth.

*Color code* (*one year or older*).—P1.46 I5 — Old Mauve (immature) P1.7 H6 —Peony B.

*Lenticels.*—Moderate number on branch. Size — small — 1 mm–2 mm (0.04–0.08 inch).

Leaves:

*Size.*—Normal for apricot and alternate.

*Length.*—2.45–3.35 inch (63–85 mm).

*Width.*—1.89–2.52 inch (48–63 mm).

*Shape.*—Obovate with acuminate apex.

*Color code.*—Upwardly disposed surface — P1.24 H12 Near Chrome Gr. Deep for younger leaves — terminal leaf tips — P1.6 L3 — Pomegranate; some of the younger leaves have reddish color on the edges. Downward disposed surface — P1.21 L6 Parrot Green.

*Margin.*—serrate.

*Venation.*—Pinnate.

*Leaf vein.*—Color code P1.18 J7 —near Spring gr. Thickness 0.81 inch (2 mm).

*Glandular characteristics.*—None.

*Petiole.*—Medium. Length. — 1.97–2.17 inch (50–55 mm). Thickness — 2 mm (0.08 inch). Color Code — P1.18 J5 Sky green.

*Stem glands.*—Small ovate. Position — on one side of stem. Pattern — sparse on younger stems. Color Code —P1.22 I5 Sage Green.

*Stipules.*—Small — 1.2 mm (0.04–0.08 inch). Color Code — P1.7 H9 Liverbrown and autumn oak.

Flowers:

*Flower buds.*—Moderately hardy for Central California climate. Shape — conic, clusters of two to three. Size — Length 7–5 mm (0.30 inch). Width — 7.3 mm (0.287 inch). Color — white — P1.1 A1. Calyx — 5 sepals — Color Code — P1.17 I6 Viridine gr.

*Flowers — about* 75% full bloom by February 23rd. Abundant and showy, perfect flowers. Size — medium. Diameter — 22–26 mm (0.87–1.02 inch). Petals 5 — broadly ovate width — 8–9 mm (0.31–0.354 inch). length — 10–11 mm (0.39–0.43 inch). edge — undulate.

*Claw.*—Small — 1 mm (0.04 inch).

*Pedicel.*—8–10 mm (0.31–0.39 inch). Color Code — P1.17 I6 Viridine gr.

*Pistil* 1.—7–8 mm (0.28–0.31 inch). Stamens — 25–28.

*Filament.*—Length 5–8 mm (0.30–0.35 inch).

*Anther Small.*—1 mm (0.04 inch). Color Code— P1.13 L11 Peruvian Br.

Fruit:

*Date of maturity.*—May 11–14, 2005. Size — medium — 6 fruit avg. 3¼ oz. (approx. 91 grams). Diameter Axial Plane — 2⁵⁄₃₂ inch) (54.8 mm). Transverse in Suture Plane — 1³¹⁄₃₂ inch (50 mm). Transverse in Right Angles to Suture Plane — 2⅛ inch (54 mm).

*Form.*—Nearly uniform. Symmetrical or asymmetrical — nearly symmetrical — slightly oblong. Suture — distinct groove extending from base to apex with deep groove at the apex or stem cavity. Ventral Surface — rounded lipped both sides. Stem Cavity — Width 11 mm (0.43 inch). Depth 14 mm (0.55 inch). Length 13 mm (0.51 inch). Shape — elongated. Stem — short — ¼ inch (6.2 mm). Caliper — ⅜ inch (9.525 mm). Apex — rounded. Pistil Point — negligible. Skin — Thickness — medium. Texture — smooth. Tendency to Crack — moderate in wet weather.

*Color code.*—Blush color P1. 4 L10 Holly Berry. Ground color P1.3 H10 Coral Bell. Flesh Color P1.4 G10 —Araby. Color of Surface. — P1.5 H9 Near athenia faded rust. Color of Pit Well — P1.7 L12 Caldera.

*Juice production.*—Moderate.

*Flavor.*—Amygdalin moderate.

*Aroma.*—Slight to moderate.

*Texture.*—Firm.

*Fibers.*—Moderate numbers and coarse.

*Ripening.*—Slightly uneven, first near apex.

*Eating quality.*—Very good Stone.

*Clingstone, Freestone or Semi-Freestone.*—Freestone.

*Fibers.*—Number many. Length — 5–11 mm (0.197–0.43 inch).

*Size.*—Length 1.25–1.30 inch (32–33 mm). Width — 0.91–1.02 inch (23–26 mm). Thickness — 0.45–0.52 inch (11–13 mm).

*Form.*—Ovate.

*Hilium.*—4–5 mm (0.16–0.20 inch) long.

*Apex shape.*—Broadly cuneate.

*Color code* (*dry*).—Honey Middlestone is P1.12 J6.

*Base.*—Rounded, cupped at the Hilium.

*Sides.*—Nearly equal.

*Ridges.*—Apex to base on ventral side.

*Tendency to split.*—Not known.

*Use.*—Fresh market.

*Keeping & shipping.*—Quantity.

*Resistance to disease.*—Unknown.

*Harvesting.*—May 12–14, 2005.

*Name of the new variety.*—'GA 10F'.

What is claimed is:

1. A new and distinct variety of apricot tree having characteristics described and illustrated herein.

* * * * *